United States Patent
Lahti

(10) Patent No.: US 7,364,576 B2
(45) Date of Patent: Apr. 29, 2008

(54) METHOD AND ASSEMBLY FOR TREATING PAIN OF LIQUID NITROGEN THERAPY

(76) Inventor: James Lahti, 660 Elder La., Winnetka, IL (US) 60093

( * ) Notice: Subject to any disclaimer, the term of this patent is extended or adjusted under 35 U.S.C. 154(b) by 639 days.

(21) Appl. No.: 10/763,287

(22) Filed: Jan. 26, 2004

(65) Prior Publication Data
US 2004/0230261 A1    Nov. 18, 2004

Related U.S. Application Data

(60) Provisional application No. 60/442,121, filed on Jan. 24, 2003.

(51) Int. Cl.
*A61B 18/02*    (2006.01)
(52) U.S. Cl. ...................................... 606/20
(58) Field of Classification Search ............. 606/20–26
See application file for complete search history.

(56) References Cited

U.S. PATENT DOCUMENTS

| | | | |
|---|---|---|---|
| 5,415,866 A * | 5/1995 | Zook | 424/448 |
| 5,976,505 A | 11/1999 | Henderson | |
| 6,306,119 B1 | 10/2001 | Weber et al. | |
| 6,503,246 B1 * | 1/2003 | Har-Shai et al. | 606/23 |

OTHER PUBLICATIONS

Rothman, Karen F., Current Opinion in Pediatrics, 1995, vol. 7, pp. 415-422, "Minimizing the pain of ofice procedures in children".*

* cited by examiner

*Primary Examiner*—Roy D. Gibson
(74) *Attorney, Agent, or Firm*—Kelley Drye & Warren, LLP

(57) ABSTRACT

Several embodiments of a method for treating pain associated with liquid nitrogen therapy and an assembly are disclosed. The method comprises comprising the steps of administering liquid nitrogen to an epidermal lesion; and applying a topical anesthetic to the epidermal lesion during or after a thaw cycle of liquid nitrogen to achieve anesthesia.

6 Claims, 1 Drawing Sheet

METHOD AND ASSEMBLY FOR TREATING PAIN OF LIQUID NITROGEN THERAPY

CROSS-REFERENCE TO RELATED APPLICATIONS

The present invention relates to, and is entitled to the benefit of the earlier filing date and priority of, application Ser. No. 60/442,121, filed on Jan. 24, 2003, which is herein incorporated by reference as if fully set forth.

FIELD OF THE INVENTION

The present invention relates to the use of topical anesthetics. More particularly, the present invention relates to the novel use of a topical anesthetic in conjunction with liquid nitrogen therapy.

BACKGROUND OF THE INVENTION

The skin is an anatomical and physiological boundary critical to the survival of an individual. The skin is composed of two layers, the dermis and the epidermis. The dermis is a deeper layer of the skin giving the skin mechanical strength. In contrast, the epidermis is superficial and is the body's primary barrier to the environment. Multiple superficial lesions may develop in the epidermis. These lesions are usually removed by common, outpatient procedures.

Examples of very common epidermal lesions include verruca vulgaris (warts), actinic keratosis (precancerous lesions on the skin), and seborrheic keratosis (benign overgrowths). Less common but still significant lesions include basal cell carcinomas, squamous cell carcinomas, and malignant melanoma. Most epidermal lesions form through neoplasia (cancers) or hyperplasia (overgrowth of normal cells).

Typical treatments for epidermal lesions are based on excision, destruction and immunomodulation (modifying the immune system to cause self elimination). Excision is the removal by cutting. Destruction may be accomplished through liquid nitrogen therapy (freezing), curettage (a form of scraping the lesion off), electrodessication (essentially burning the lesion with an apparatus that creates a spark), and lasers (causing vaporization of the lesion). Immunomodulation is accomplished by using chemicals such as 5-fluorouracil, imiquimod, tretinoin, etc., to create or modify an immune response to treat specific lesions.

All of the treatment modalities have the risk of pain, bleeding, infection, recurrence, and scarring. The decision as to which treatment to use is based on the nature of the lesion (benign or malignant), the number of lesions, the location of the lesion, the age of the patient, and co-morbid conditions in the patient.

In particular, liquid nitrogen is a common method of destruction as it is easy to perform on an outpatient basis and is usually effective. The specialties that use the procedure the most include dermatologists, pediatricians, family practitioners, and internists. The main complication or common side effects of liquid nitrogen therapy include pain associated with the procedure, blistering, swelling, ulceration, discoloration, infection, and scarring.

These types of discomfort can cause significant psychological distress in patients, particularly children. Typically, liquid nitrogen therapy causes two types of pain: one, an immediate pain associated with the freezing process of the skin; and two, a delayed pain that occurs during and after the thaw cycle. The post-thawing pain frequently is the most painful and can last for hours.

One of the benefits of liquid nitrogen therapy is that it can be used on the general population. The limitations of the therapy are that it is difficult to judge the depth of the freezing necessary, and that there is pain associated with the therapy. There may be some limits to the size of lesions that can be frozen, but as of yet, there are no established guidelines in that regard.

In order to ameliorate the pain associated with liquid nitrogen therapy, topical anesthetics are used. These topical anesthetics may contain, but are not limited to, lidocaine, eutectic mixtures of lidocaine and prilocaine, liposomal lidocaine, and lidocaine with AcidMantle® vehicle. The recommended and manufacturer directed use of these anesthetics is local application with or without occlusion 30-60 minutes prior to any procedure to achieve any anesthetic effect.

The use of topical anesthetics prior to the use of liquid nitrogen, however, has limited efficacy in relieving pain. This is due in part to the hyperkeratotic nature of the lesions treated. Hyperkeratotic lesions have a thickened stratum corneum (the tough, impermeable, outermost layer of the epidermis). An example of this type of lesion is a wart. This thickness likely prevents the diffusion of any anesthetic from the surface of the skin into the deeper layers where it would exert its effect.

What is needed therefore is a method of using liquid nitrogen therapy that diminishes the amount of pain that a patient may incur with the treatment of an epidermal or cutaneous lesion by liquid nitrogen. In particular, a method is needed to reduce or diminish the pain a patient experiences during and after the thawing cycle of the liquid nitrogen therapy.

It is therefore an advantage of some, but not necessarily all, embodiments of the present invention to provide a novel method for the relief of pain associated with the use of liquid nitrogen for the treatment of epidermal or cutaneous lesions.

In particular, none of the above-mentioned approaches recognize the extent of pain following the thawing cycle of liquid nitrogen therapy as illuminated in the present invention, which is briefly outlined in the following Summary of the Invention, and more fully described in the Detailed Description.

Additional advantages of various embodiments of the invention are set forth, in part, in the description that follows and, in part, will be apparent to one of ordinary skill in the art from the description and/or from the practice of the invention.

SUMMARY OF THE INVENTION

Responsive to the foregoing challenges, Applicant has developed an innovative method for the treatment of pain associated with the application of liquid nitrogen therapy to epidermal or cutaneous lesions. An embodiment of the present invention is a method for the treatment of epidermal lesions with liquid nitrogen therapy comprising the steps of administering liquid nitrogen to an epidermal lesion; and applying a topical anesthetic to the epidermal lesion during or after a thaw cycle of liquid nitrogen to achieve anesthesia.

It is to be understood that both the foregoing general description and the following detailed description are exemplary and explanatory only, and are not restrictive of the invention as claimed.

BRIEF DESCRIPTION OF THE DRAWINGS

In order to assist the understanding of this invention, reference will now be made to the appended drawing, in which like reference characters refer to like elements.

DETAILED DESCRIPTION OF EMBODIMENTS OF THE INVENTION

Figure 1:
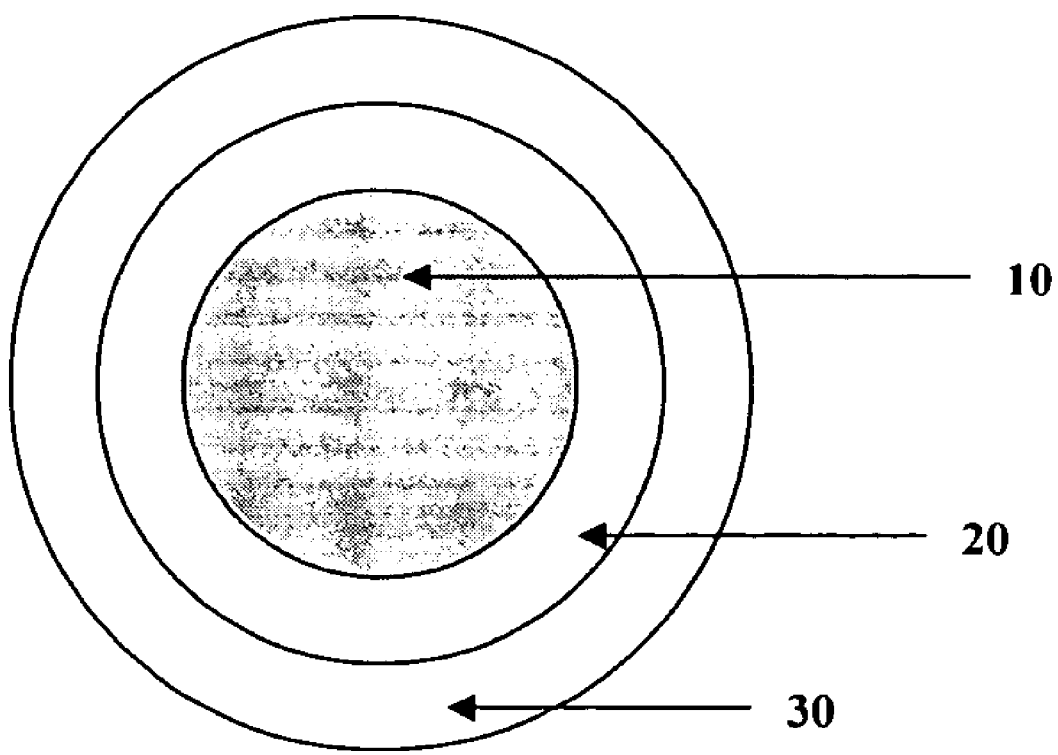
FIG. 1 is a perspective view of a lesion treated with liquid nitrogen and a topical anesthetic.

Reference will now be made in detail to embodiments of the present invention, an example of which is illustrated in the accompanying drawing.

In carrying out liquid nitrogen therapy on an epidermal lesion according to an embodiment of the present invention, both liquid nitrogen and topical anesthetic are used to diminish the pain associated with and after the thawing of the liquid nitrogen phase. Liquid nitrogen is administered either by spray application or by cotton swab or appropriate applicator. Liquid nitrogen is nitrogen gas that has been cooled to the temperature of about −195° C. When sprayed, a reservoir is most commonly used. When the nitrogen evaporates in an enclosed container, it generates pressure. This gas is then sprayed in a controlled fashion across an epidermal lesion, freezing it. The site to be treated is usually frozen to a margin of at least 2 mm, with a freeze cycle of 15 seconds or more. After thawing, a second freeze cycle may be performed. With freezing, the lesion will generally "frost", meaning that ice crystals can be seen. The amount of liquid nitrogen used depends on the size and thickness of the site to be treated, as well as the desired length of time the lesion is to be frozen, and is known to one of ordinary skill in the art.

According to an embodiment of the present invention, the topical anesthetic is applied following the liquid nitrogen, near the end of the thaw cycle, or shortly after the lesion has finished thawing. With reference to FIG. 1, following freezing by liquid nitrogen, a topical anesthetic is applied to an epidermal lesion 10 with a margin of about 2 mm (millimeters) or more 20. Essentially, any appropriate applicator can be used including, but not limited to, a cotton swab. The amount of topical anesthetic used is enough to cover the treatment area and about 2 mm beyond 30 (this is usually less than 1 mg (milligram)). According to an embodiment, the topical anesthetic should cover the treatment site and about 2 mm beyond the extent of the freezing. Repeated applications of the topical anesthetic can be performed if there is any breakthrough pain after the initial application.

The method of applying the topical anesthetic after liquid nitrogen application and thawing of the skin and/or lesion should be effective with any of the known topical anesthetics in the formulations and strengths provided by the manufacturer. The anesthetics may have the following components, but are not limited to: lidocaine, lidocaine and prilocaine in a eutectic mixture (ex., EMLA®), liposomal lidocaine (ex. LMX-4®, LMX-5®), lidocaine in an AcidMantle® vehicle (ex. LidaMantle®) or any other appropriate components contained in a topical anesthetic. Manufacturer supplied strengths may vary from about 2% to about 5% anesthetic depending on the product.

Numerous characteristics and advantages have been set forth in the foregoing description, together with details of structure and function. The novel features are pointed out in the appended claims. The disclosure, however, is illustrative only, and changes may be made in detail, especially in matter of shape, size, and arrangement of parts, within the principle of the invention, to the full extent indicated by the broad general meaning of the terms in which the appended claims are expressed.

What is claimed is:

1. A method for the treatment of epidermal lesions with liquid nitrogen therapy, comprising the steps of:
    administering liquid nitrogen to the epidermal lesion; and
    applying a topical anesthetic to the epidermal lesion and the surrounding epidermis following the administration of the liquid nitrogen.

2. The method of claim 1, wherein the step of applying the topical anesthetic occurs during the thawing of the epidermal lesion.

3. The method of claim 1, wherein the step of applying the topical anesthetic occurs after the thawing of the epidermal lesion.

4. The method of claim 1, further comprising the step of relieving the pain associated with the thawing of the epidermal lesion.

5. The method of claim 4 wherein the relief of pain occurs in about fifteen seconds following application of the topical anesthetic.

6. A method for the treatment of epidermal lesions with liquid nitrogen therapy, comprising the steps of:
    administering liquid nitrogen to the epidermal lesion; and
    applying a topical anesthetic to the epidermal lesion and the surrounding epidermis following the administration of the liquid nitrogen and during the thawing of the epidermal lesion.

* * * * *